(12) United States Patent
Moore (10) Patent No.: US 6,918,391 B1
(45) Date of Patent: Jul. 19, 2005

(54) MULTI-LUMEN ENDOTRACHEAL TUBE

(76) Inventor: Johnny V. Moore, 2604 Drennen Pl., Birmingham, AL (US) 35242-4624

( * ) Notice: Subject to any disclaimer, the term of this patent is extended or adjusted under 35 U.S.C. 154(b) by 425 days.

(21) Appl. No.: 10/151,340

(22) Filed: May 20, 2002

(51) Int. Cl.[7] .................................................. A61F 6/02
(52) U.S. Cl. ............. 128/842; 128/207.14; 128/207.15; 128/911; 600/116; 600/120; 600/158
(58) Field of Search ........................... 128/842, 207.14, 128/207.15, 207.16, 911, 207.17, 207.18, 200.14, 200.26, 912; 600/115, 116, 120, 153, 156, 158, 529, 484, 549, 586; 604/96.01, 264, 164.01

(56) References Cited

U.S. PATENT DOCUMENTS

| | | | | |
|---|---|---|---|---|
| 4,150,676 A | * | 4/1979 | Jackson ................. | 128/207.18 |
| 5,067,497 A | * | 11/1991 | Greear et al. .......... | 128/207.15 |
| 5,697,365 A | * | 12/1997 | Pell ........................ | 128/207.15 |
| 5,937,858 A | * | 8/1999 | Connell ................. | 128/207.14 |
| 5,964,223 A | * | 10/1999 | Baran .................... | 128/207.14 |
| 5,976,072 A | * | 11/1999 | Greenberg ............. | 600/120 |
| 6,164,277 A | * | 12/2000 | Merideth ............... | 128/207.14 |
| 6,390,094 B1 | * | 5/2002 | Slionski ................. | 128/207.16 |
| 6,568,393 B2 | * | 5/2003 | Christopher ........... | 128/207.14 |
| 6,672,308 B1 | * | 1/2004 | Gaspari ................. | 128/207.14 |
| 6,698,428 B2 | * | 3/2004 | Brain .................... | 128/207.14 |

\* cited by examiner

Primary Examiner—Fadi H. Dahbour
(74) Attorney, Agent, or Firm—Smith, Gambrell & Russell (57) ABSTRACT

A multi lumen endotracheal tube having a balloon cuff to seal a patient's trachea during intubation. The ET tube having a main lumen for the exchange of respiratory and medicinal gases consequent to a medical procedure, a secondary lumen for inflation of the balloon cuff, and a tertiary lumen for transmission of sound waves via air medium contained therein, permitting auscultatory monitoring of a patient's breath sounds during intubation and subsequent monitoring of cardiac and respiratory activity after sealing of the ET tube. The ET tube is particularly a adapted for utilization by an anesthetist by including temperature sensor to permit remote monitoring of body core temperature and body cavity ausculation of cardiac and respiratory activity.

7 Claims, 8 Drawing Sheets

MULTI-LUMEN ENDOTRACHEAL TUBE

TECHNICAL FIELD

This invention relates to the field of endotracheal tubes having an inflatable cuff to seal a patient's trachea during intubation. More specifically, the device of the present invention is directed to an endotracheal tube adapted for ausculatory monitoring of a patient's breath sounds. With even greater particularity the device may be adapted for utilization by an anesthetist to permit remote monitoring of body core temperature and body cavity ausculation of cardiac and respiratory activity.

BACKGROUND OF THE INVENTION

Multi lumen inflatable cuff endotracheal (ET) tubes are well known in the medical arts particularly with respect to anesthesiology. Endotracheal tubes of this type will generally comprise a main lumen to maintain a patient's airway for the passage of respiratory gases to and from the lungs and a secondary lumen for inflation of the balloon cuff after the health care provider has intubated the patient. The inflatable cuff performs various functions including: securing a seal within a patient's tracheal, isolating the upper and lower trachea to prevent the deleterious passage of body fluids into the lungs, and permitting cyclic pressurization of a patient's lungs by a ventilator. U.S. Pat. No. 5,697,365, issued to Pell is typical of multi lumen inflatable cuff ET tubes in the art.

Inflatable cuff ET tubes may also include a tertiary lumen, for performing various functions. For example, U.S. Pat. No. 5,067,479, issued to Greear et al., discloses a tertiary lumen for suctioning bodily fluids from above the balloon cuff. U.S. Pat. No. 4,150,676, issued to Jackson, discloses an inflatable cuff ET tube which provides directional control over the tip of an ET tube by manipulation of a filament carried in a tertiary lumen. The directional control provided facilitates intubation of the device by an anesthetist or health care provider.

Another aspect related to the use of multi lumen ET tubes is proper insertion and positioning of the ET tube within the patient's trachea. U.S. Pat. No. 6,164,277, issued to Meredith, discloses the use of an audio guided intubation stylet to assist the practitioner with intubating "difficult" airways. Meredith discloses a stylet comprising a microphone that transmits breath sounds to an external speaker. By relying on the breath sounds, the practitioner can ensure intubation of the stylet into the trachea rather than the esophagus. The properly placed stylet is then used as guide tube for subsequent insertion of the ET tube. Once the ET tube is positioned, the stylet may then be removed. Merdeth also discusses the limitations of optically guided methods of intubation, citing their complexity, high cost, limited availability and limited usefulness when significant amounts of bodily fluids are present during intubation.

Multi lumen ET tubes have also been introduced which provide for the monitoring and management of critical physiological parameters. U.S. Pat. No. 5,937,858, issued to Connell, discloses a multi lumen ET tube in which tertiary lumina carry sampled gasses to external analyzers to determine respiratory gas concentrations. Similarly, U.S. Pat. No. 5,964,223, issued to Baran, discloses a nebulizing catheter for insertion into an ET tube for the delivery of medication in closer proximity to the lungs. Baran also discloses the use of removable catheters to carry sensors for monitoring various physiological parameters for nebulizer control and anesthetist monitoring. Accordingly, while the prior art demonstrates distinct improvements in ET tube capabilities the increasing complexity of these improvements have resulted in a concomitant increase in their cost and reduction in their availability.

Similarly, despite the numerous improvements in the art, anesthetists are still required to insert multiple tubes or catheters into a patient for airway management and patient monitoring purposes. In practice, body core temperature is typically received from a temperature sensor incorporated in a separate esophageal tube. Therefore, in addition to intubating the patient with an ET tube, the anesthetist must also insert a separate esophageal tube. Regardless of insertion order, the insertion of one tube will make the subsequent insertion of the other tube more difficult, particularly when the targets of the respective tubes are incompatible.

The requirements of stocking, maintaining and utilizing multiple devices for a single procedure further contributes to the complexity and cost of the procedures. Similarly, the high cost and complexity of optical and electronic audio guidance mechanisms necessitates that their use be limited to "difficult" airway management cases.

Accordingly, there is a need in the art for reducing the number and complexity of devices required to accurately intubate a patient and effectively monitor patient physiological parameters.

BRIEF SUMMARY OF THE INVENTION

An object of the present invention is to provide an endotracheal tube that facilitates one's ability to ventilate the lungs monitor heart sounds, breath sounds and temperature. Such an ET tube would enjoy greater application, particularly in field conditions where the necessary electronic support equipment may not be available.

A second object of the invention is to provide an ET tube which integrates temperature sensing means for monitoring a patient's body core temperature. Such an arrangement would eliminate the requirement to insert a separate esophageal tube for taking such measurements.

Accordingly, the ET tube of the present invention comprises an elongated tubular member having a main lumen, a secondary lumen, and at least one tertiary lumen. The main lumen has a substantially larger transverse area than the secondary and tertiary lumina and is primarily utilized for the exchange of respiratory gases. The secondary lumen communicates an air source to an inflatable cuff located on a distal end of the ET tube, which is received in a patient's airway during intubation. Upon inflation, the cuff seals the trachea in order to generate positive pressure and protect the lungs from aspiration.

An ausculatory receiver is provided on the distal end of the ET tube. The ausculatory receiver comprises an elongate arcuate disk having a plurality of apertures spaced apart thereon. A diaphragm overlying the arcuate disk receives sound waves and transmits the source to an air medium contained in a chamber defined subjacent the diaphragm. The sound waves are transmitted through an air medium in the tertiary lumen for reception and monitoring by an external monitoring device. The health care practitioner may then monitor the transmitted sound waves by an external ausculation device, such as a stethoscope coupled to the tertiary lumen at a proximal end of the ET tube external the patient's body.

To provide the health care practitioner the ability to monitor a patient's body core temperature, the ET tube of the present invention is provided with a temperature sensor, such as a thermistor. The temperature sensor extends into the subjacent cavity of the auscultatory receiver. The conductors for the temperature sensor are received in a tertiary lumen for communicating the temperature signals to the proximal end of the ET tube. A connector is provided external the ET tube for coupling the temperature sensor to signal conversion and display means apart from the ET tube.

BRIEF DESCRIPTION OF THE DRAWINGS

Various embodiments of my invention are depicted in the appended drawings which form a part of this disclosure and wherein.

DETAILED DESCRIPTION OF THE INVENTION

In reference to the several drawings the multi lumen endotracheal tube 10 of the present invention comprises a longitudinally extending tubular member 11, having a proximal portion 12, and a distal portion 13. Distal portion 13, refers to that portion of ET tube 10 which is inserted ed into a patient's body cavity during intubation, while proximal portion 12 refers to that portion of ET tube 10 which remains external the patient's body. A balloon cuff 21 circumscribing a part of distal portion 13 is selectively inflatable for sealing the trachea. According to the present invention, an auscultatory receiver 25 is provided on distal portion 13 of ET tube 10 to receive a patient's breath sounds. These breath sounds are then transmitted via a fluid media through a tertiary lumen 30 for external monitoring. This arrangement offers health care providers a low cost alternative to electro-optical and electro-audio guided intubation techniques.

As is known in the art, ET tube 10 is made of a semi-rigid tubular member 11, preferably plastic, having an arch defined along its longitudinal length, such that the arch roughly conforms to the natural curvature of the oro/nasopharyngeal airway of a patient. The inner curvature of the arch defines an anterior surface 16 and the outer curvature of the arch defines a posterior surface 17. Similarly, tubular member 11 should be sufficiently flexible to facilitate intubation of a patient, yet be sufficiently rigid to avoid collapse of the various lumina after intubation.

Figure 1:
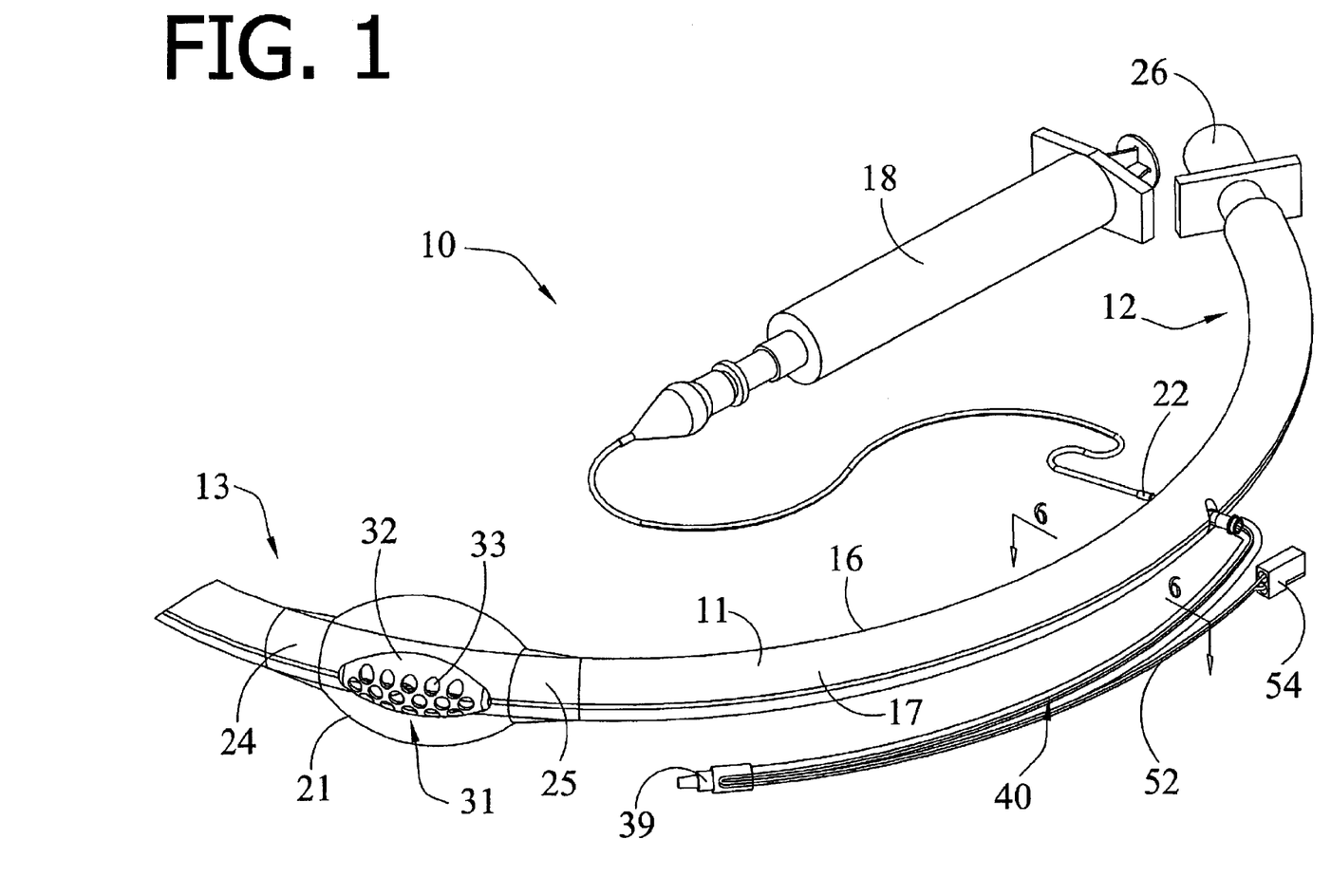
FIG. 1 is an posterior perspective view of the multi lumen endotracheal tube and cuff inflator.
Figure 2:
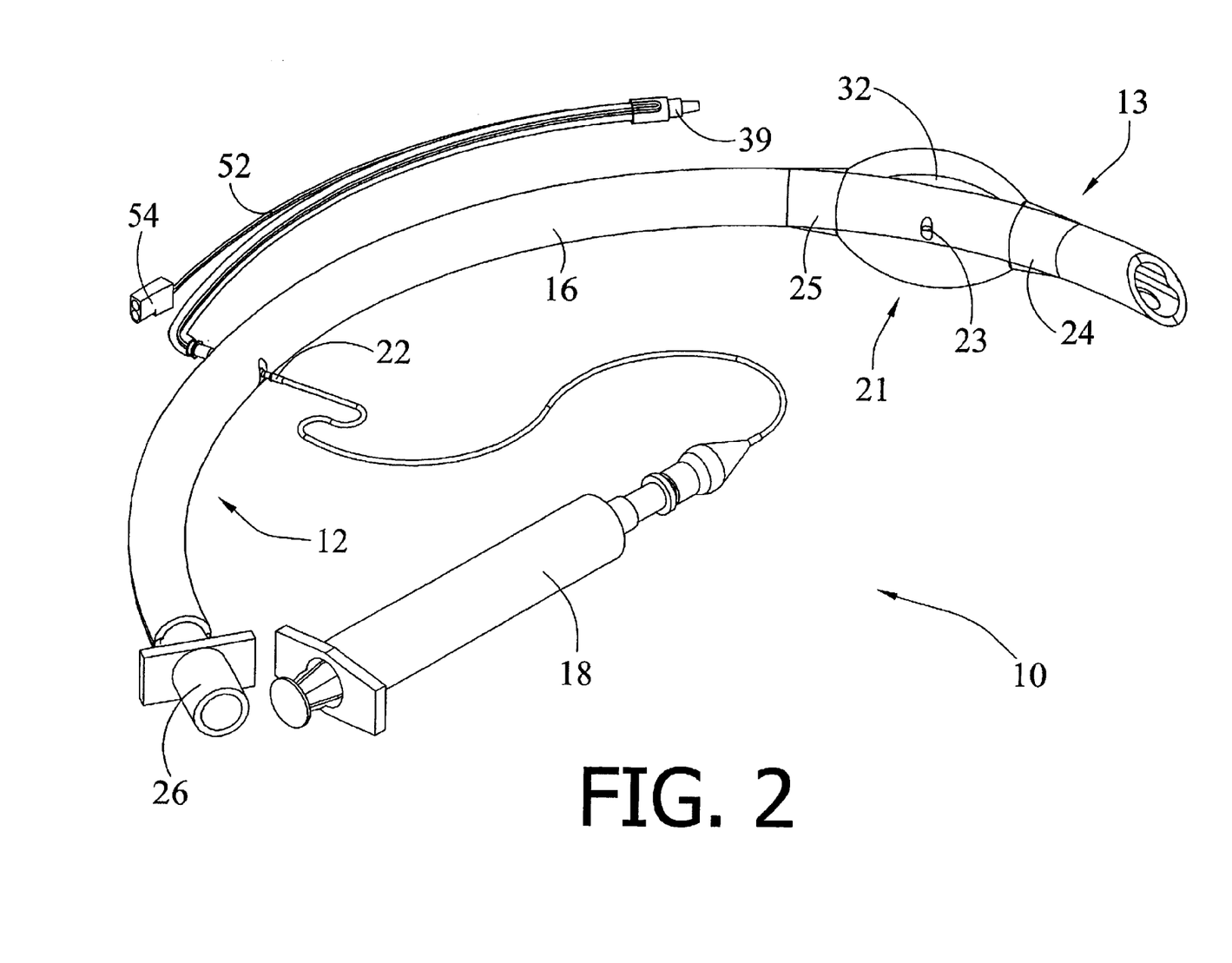
FIG. 2 is an anterior perspective view of the multi lumen endotracheal tube and cuff inflator.
Figure 3:
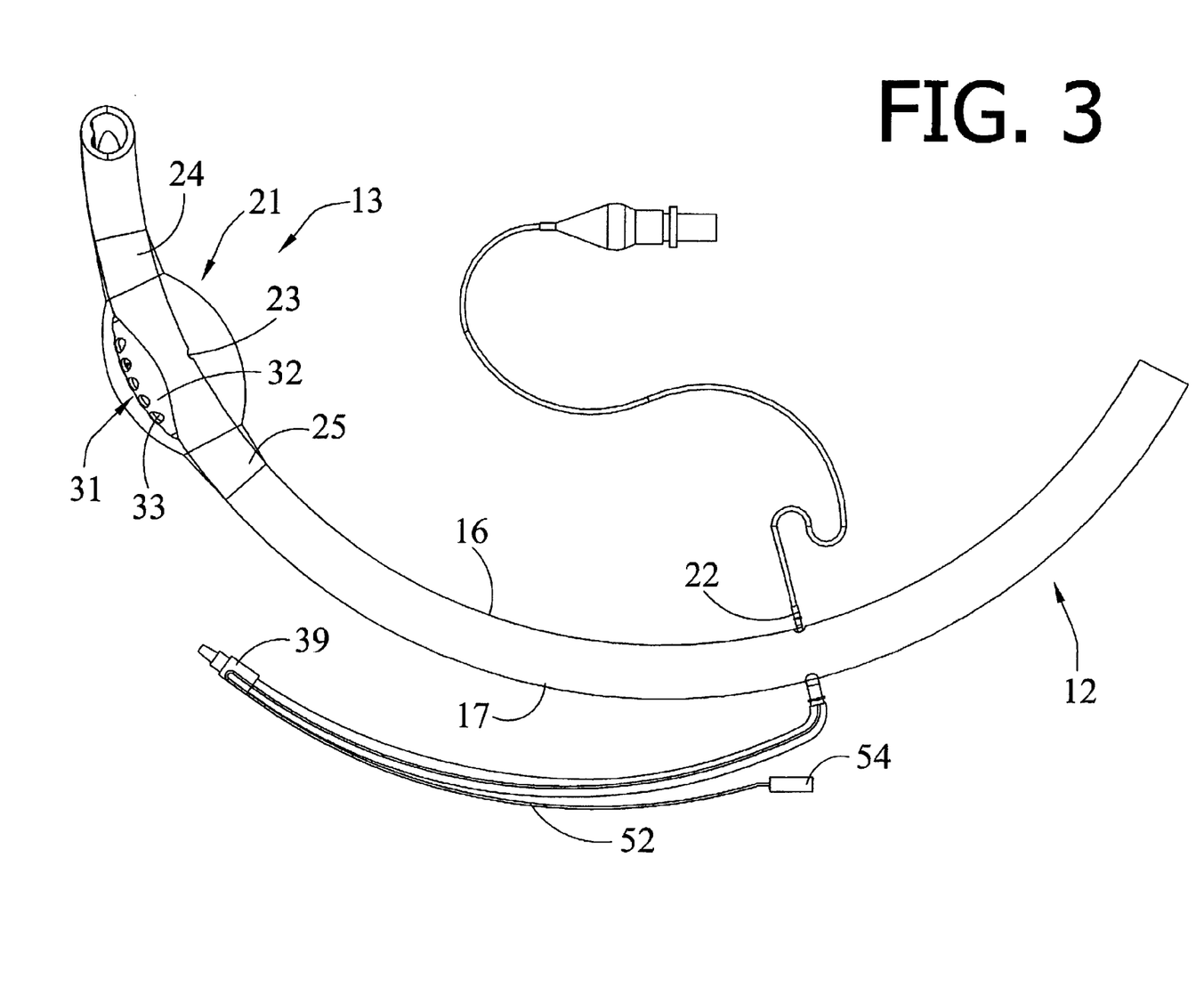
FIG. 3 is a lateral view of the multi lumen endotracheal tube and cuff inflator.
Figure 4:
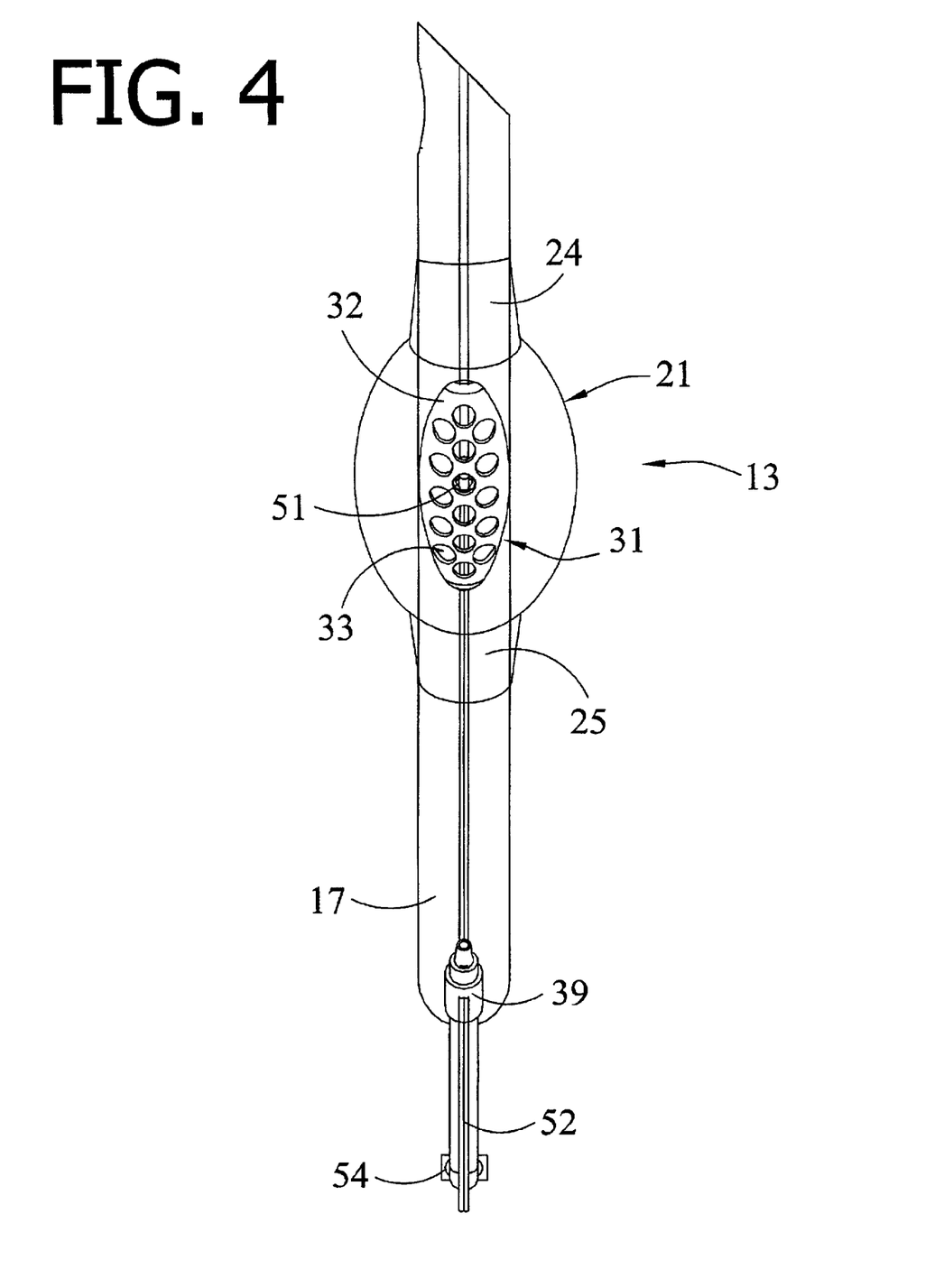
FIG. 4 is a lateral posterior view of the distal end of the multi lumen endotracheal tube.
Figure 5:
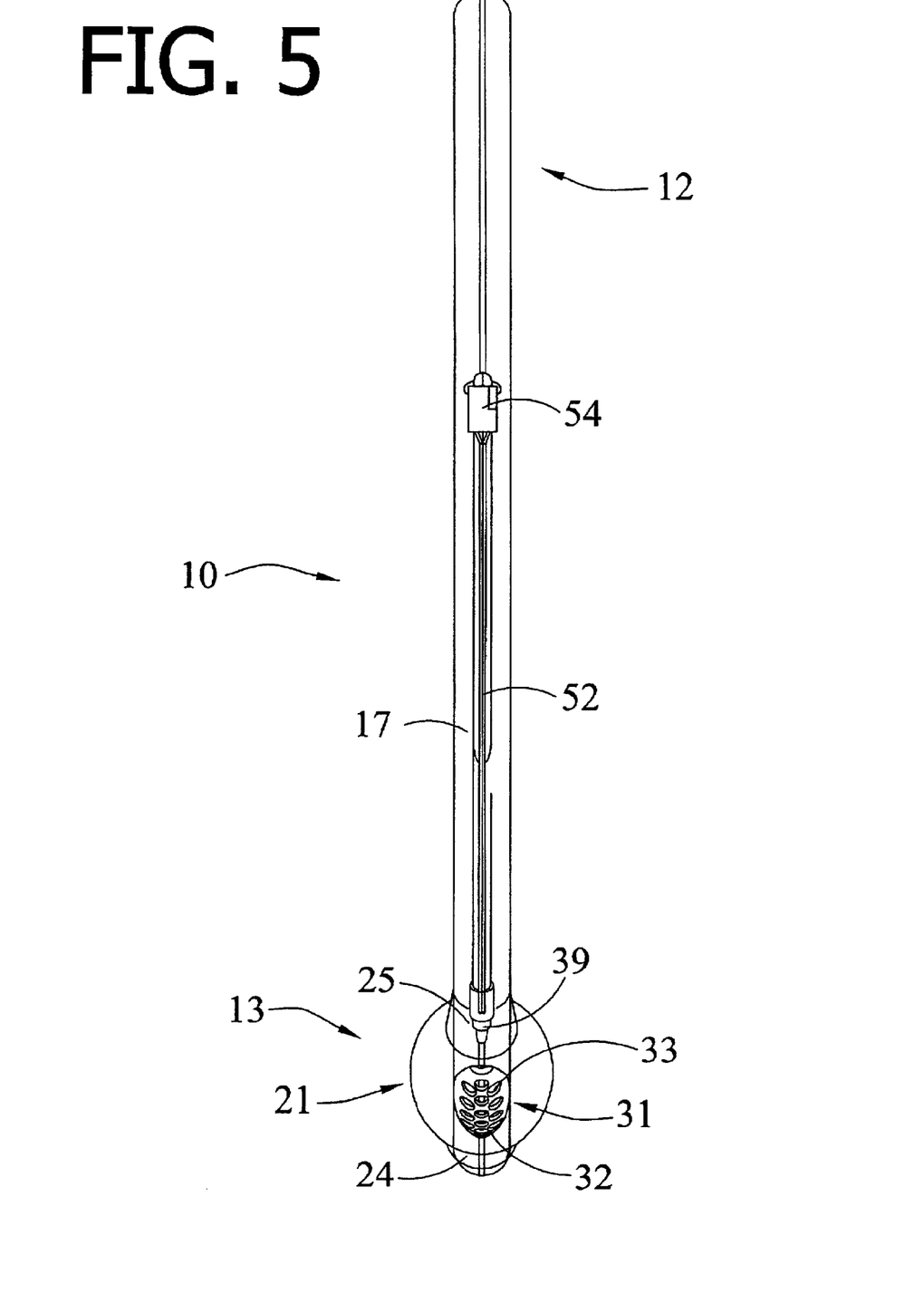
FIG. 5 is a lateral posterior view of the proximal end of the multi lumen endotracheal tube.
Figure 6:
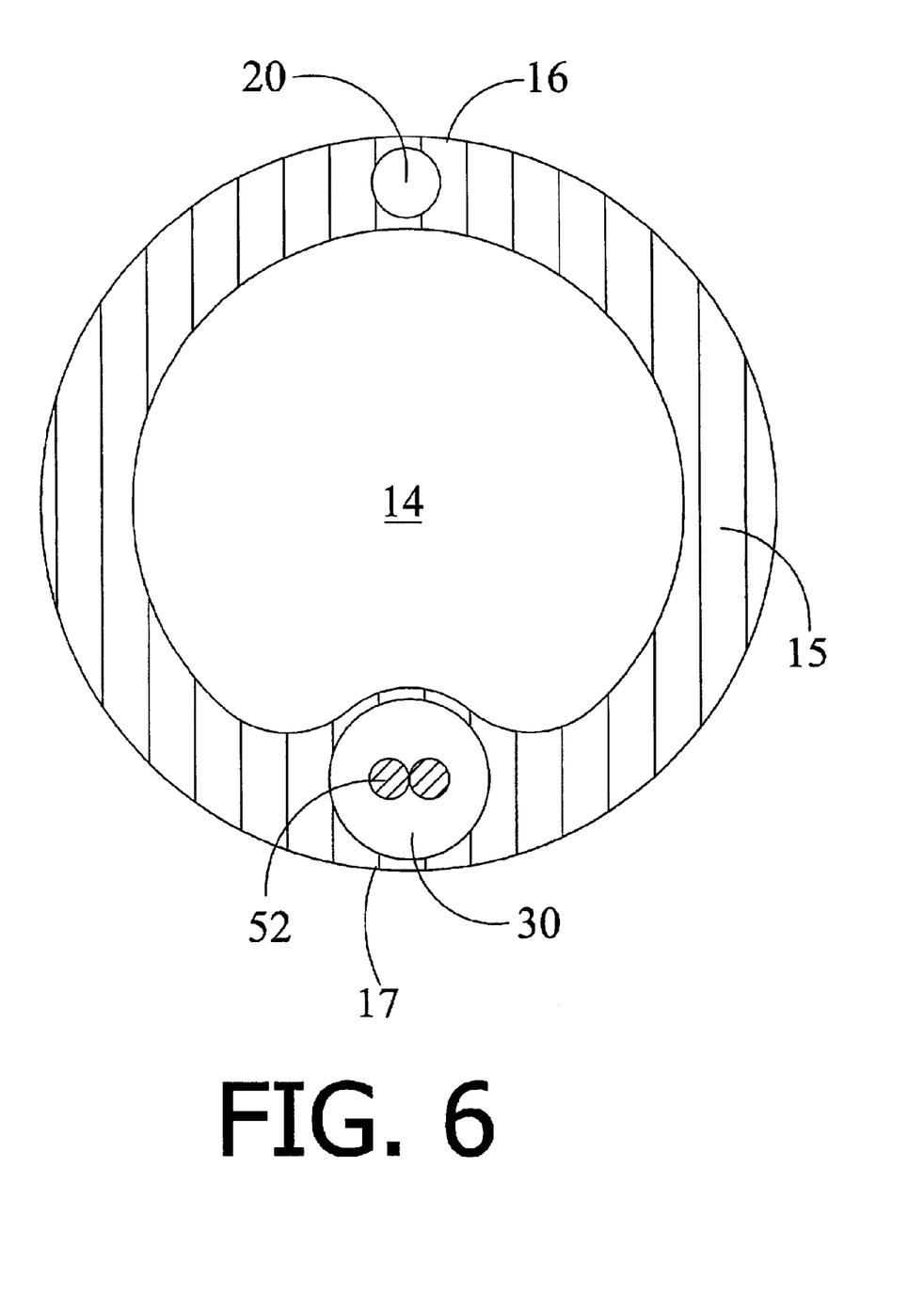
FIG. 6 is a transverse sectional view of the multi lumen endotracheal tube.

As depicted in the transverse sectional view of FIG. 6, taken along reference line 6 of FIG. 1, a wall 15 of tubular member 11 defines a main lumen 14, a secondary lumen 20 and a tertiary lumen 30. For ease of manufacture, each lumen extends throughout the longitudinal length of tubular member 11. However, the secondary lumen 20 and tertiary lumen 30 are sealed at distal and proximal ends of tubular member 11, so that entry and exit points for these lumina may be defined at desired points along tubular member 11.

Once a patient has been intubated with ET tube 10, main lumen 14 provides gas communication between a patient's lungs and a point external the patient's body. Main lumen 14 is primarily for the exchange of respiratory gases and administration of medicinal gases according to methods well known in the art. As disclosed in U.S. Pat. No. 5,964,223, issued to Baran, main lumen 14 may also serve to communicate various catheters therein. Accordingly, the transverse area of main lumen 14 will be substantially larger than that of secondary lumen 20 and tertiary lumen 30.

As is well known in the art, secondary lumen 20 selectively communicates an inflation air between a gas source 18 and balloon cuff 21. According to the present invention, an inflation nipple 22 is positioned at a desired point along proximal portion 12 and extends through wall 15 for communicating an inflation air source with secondary lumen 20. The position of inflation nipple 22 is selected so as to avoid interference with the coupling of ET tube 10 to a ventilator, accomplished by coupler 26, and to avoid interference with the patient's oro/nasal passages. A cuff inflation port 23 is defined through wall 15 between first and second sealing ends 24 & 25 of balloon cuff 21. Inflation port 22 communicates the inflation air carried through secondary lumen 20 to balloon cuff 21 for selective inflation and deflation of cuff 21.

Figure 8:
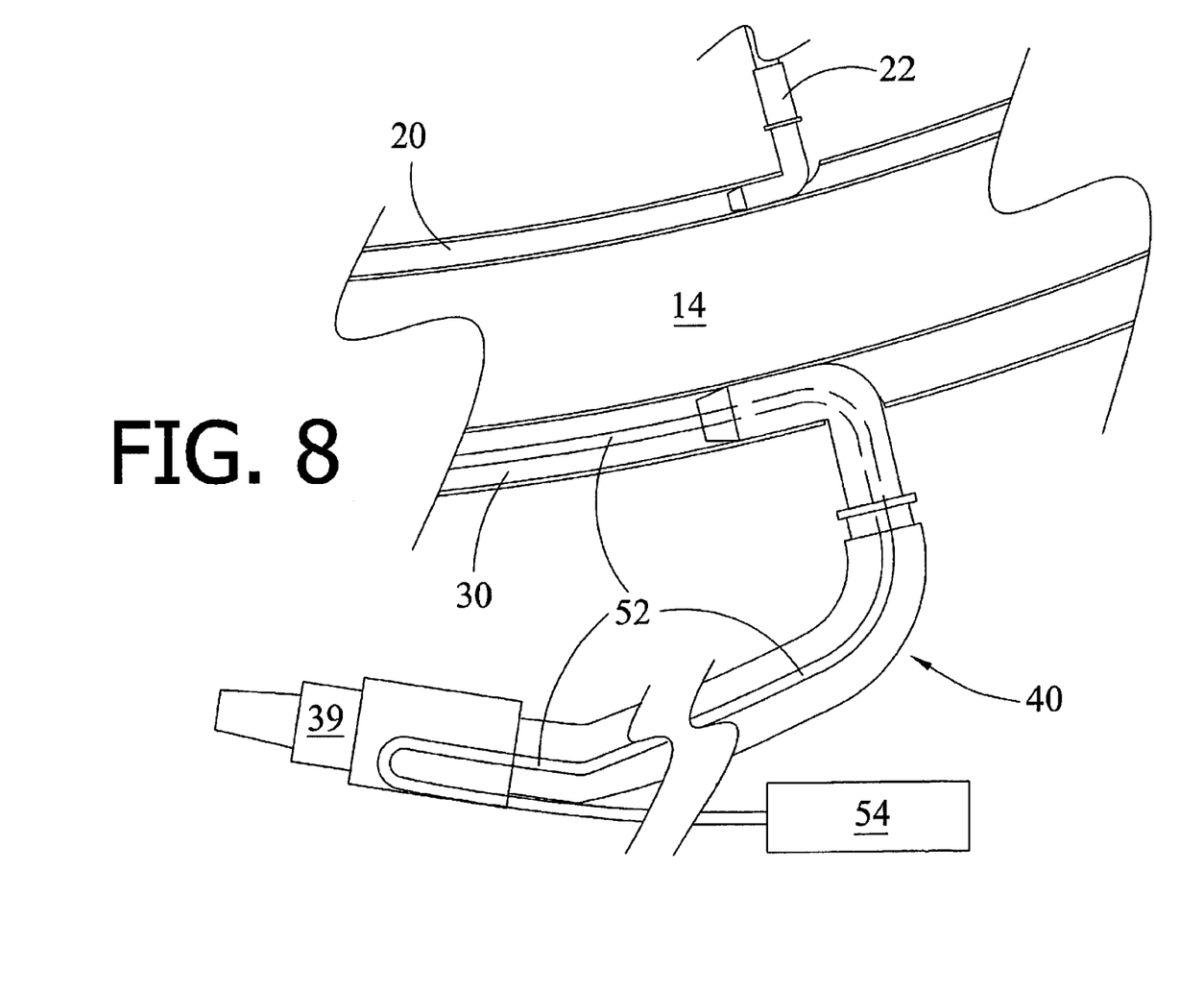
FIG. 8 is a detail longitudinal section view of the auscultation nipple.

As discussed previously, acoustic monitoring during intubation provides the health care practitioner distinct advantages over blind insertion techniques, including unimproved ET tube designs as well as optically enhanced intubation devices rendered ineffective due to the undesirable presence of excess bodily fluids. According to the present invention, a patient's breath sounds are received at an auscultatory receiver 31 carried on a distal end of tubular member 11. Auscultatory receiver 31 comprises an elongate arcuate disk 32 having a plurality of apertures 33 spaced apart therein. A diaphragm 34 superposing an outer surface 35 of arcuate disk 32 receives a patient's breath sounds thereon and transmits the same through apertures 33 to an air media contained within a chamber 36 defined subjacent diaphragm 34, an inner surface 37 of arcuate disk 32 and an outer surface 19 of tubular member 11. The air medium contained within chamber 36 communicates with the air medium contained in tertiary lumen 30 through an auscultation portal 38 defined through wall 15 of tubular member 11. The transmitted breath sounds are communicated by the air medium contained within tertiary lumen 30. As seen in FIG. 8, an auscultation tube 40 extends through wall 15 at a desired point along proximal portion 12 and communicates the transmitted breath sounds to an external monitoring device, such as a stethoscope. By this arrangement, my invention provides a simple low cost alternative to electronically guided intubation devices. Such a device may be used during all intubation procedures and not held in reserve for "difficult" airways. Moreover, since it does not rely on supporting electronic equipment, it may be utilized in field conditions. Once a patient has been intubated with my device, the practitioner may continue to monitor a patient's respiratory activity and cardiac activity.

In the preferred embodiment of my invention, auscultatory receiver 31 is enveloped by balloon cuff 21, and positioned along posterior surface 17 of tubular member 11. Containment of auscultatory receiver 31 within balloon cuff 21 is preferred for subsequent monitoring of a patient's respiratory and cardiac activity since balloon cuff 21 will insulate auscultatory receiver 31 from direct contact with the turbulent airflow that is frequently encountered near the tip 19 of distal portion 13 where the exchange of respiratory gases through main lumen 14 occurs. The advantage of positioning ausculatory receiver 31 along posterior surface 17 is that it provides improved reception of cardiac activity by its focus to the interior of the patient's body.

Figure 7:
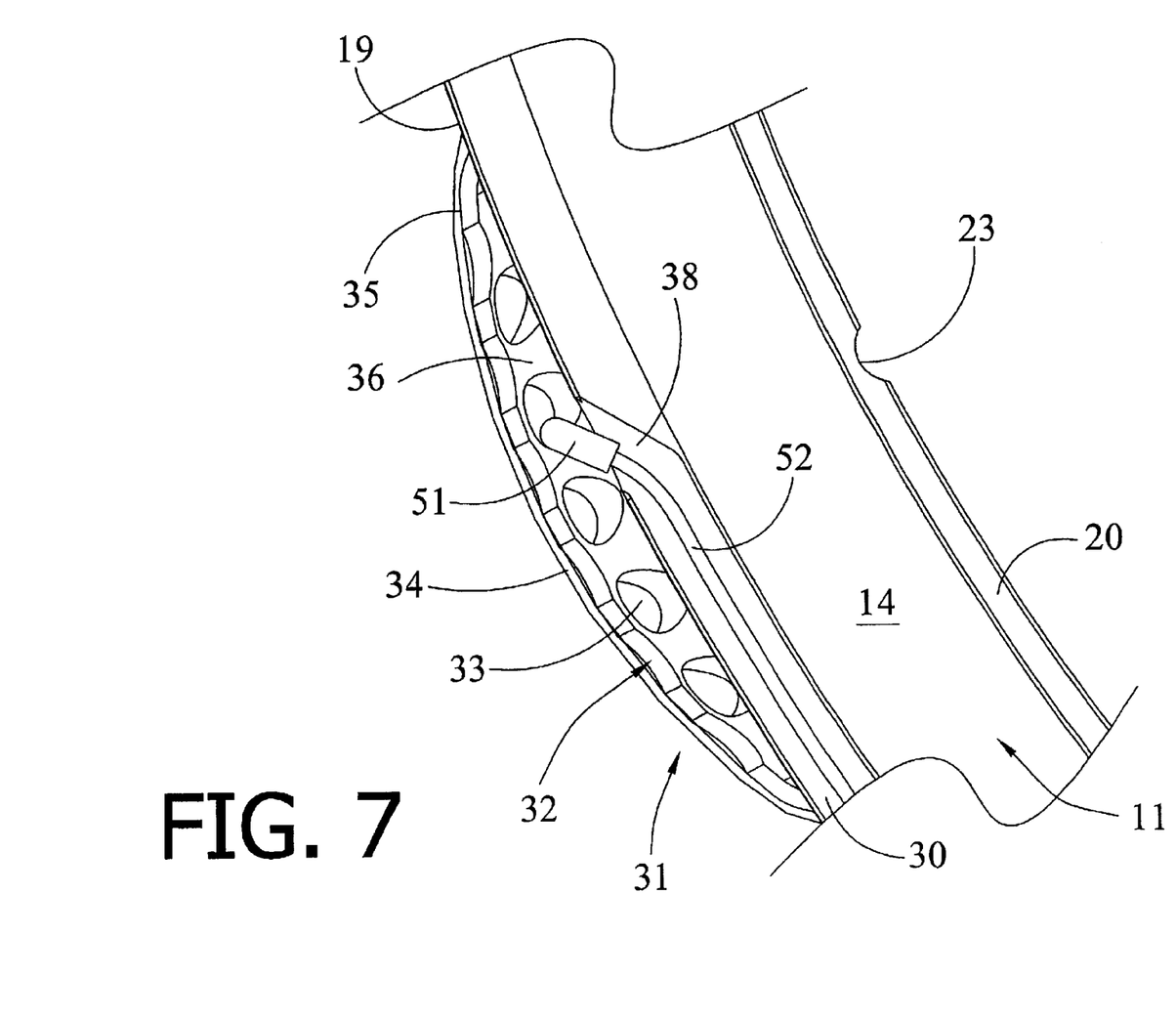
FIG. 7 is a detail longitudinal section view of the cuff area.

In addition to monitoring respiratory and cardiac activity, the ET tube contemplated by the present invention may also be equipped with temperature sensing means for monitoring a patient's body core temperature. By reference to FIG. 7, a temperature sensor 51, such as a thermistor, is shown positioned extending from ausculation portal 38 into chamber 36. Temperature sensor conductors 52 are received within tertiary lumen 30 and routed to ausculation tube 40. A nipple 39 attached to an end of ausculation tube 40, provides an exit path for conductors 52 to avoid interference between conductors 52 and connection of an external monitoring device to nipple 39. A connector 54 provides for coupling and transmission of temperature sensor 51 signals to monitoring or display means independent of ET tube 10.

Integrating temperature sensing means within ET tube 10 provides many advantages over the current practice, which requires insertion of a separate temperature sensor via an esophageal tube. Whereas the present device does not require separate insertion. A significant advantage is the reduction of cost. This is achieved by reducing the consumption of the esophageal tubes and reducing the storage and stockage levels of the same. Cost savings are also realized by decreasing the time required for the health care practitioner to perform the procedure for which intubation was indicated in the first place.

While I have described preferred embodiments of my invention, those skilled in the art will recognize that many embodiments are possible within the scope of the invention. Such variations and modifications can be made without departing from the spirit of the invention, and such variations are intended to fall within the scope of the following claims.

What I claim is:

1. An endotracheal tube for intubation within a patient's airway to prevent obstruction of the airway during a medical procedure, said endotracheal tube comprising an elongated tubular member having a proximal portion and a distal portion, said proximal portion remaining external the patient's airway and said distal portion received in the patient's airway during intubation; a main lumen defined by said elongated tubular member for exchange of respiratory gases or medicinal gases consequent said medical procedure comprising a major transverse area of said tubular member; a secondary lumen defined in a wall of said tubular member in selective communication with an air source connected to said proximal portion and a balloon cuff disposed on said distal portion for inflation of said balloon cuff; a tertiary lumen defined in said wall of said tubular member adapted to communicate a sound wave through an air medium between an ausculatory receiver disposed on said distal portion and an external ausculatory device coupled with said tertiary lumen at said proximal portion.

2. The endotracheal tube of claim 1 wherein said ausculatory receiver further comprises an elongate arcuate disk affixed to an outer surface of said tubular member, a plurality of spaced apart apertures defined in said elongate arcuate disk, a diaphragm superposed said elongate arcuate disk, and a chamber defined subjacent said diaphragm in air communication with said tertiary lumen.

3. The endotracheal tube of claim 2 wherein said ausculatory receiver is disposed between a first and a second sealing end of said balloon cuff.

4. The endotracheal tube of claim 2 wherein said ausculatory receiver is disposed on a posterior surface of said elongate tubular member.

5. The endotracheal tube of claim 1 further comprising temperature sensing means disposed on said distal portion and communicating a patient's core body temperature to said proximal portion.

6. The endotracheal tube of claim 5 wherein said temperature sensing means comprise a temperature sensor, a conductor extending between said temperature sensor and said proximal portion and a connector external said tubular member.

7. The endotracheal tube of claim 6 wherein said temperature sensor is received in said ausculatory receiver and said conductor is received in said tertiary lumen.

* * * * *